(12) United States Patent
Ahluwalia et al.

(10) Patent No.: US 6,248,751 B1
(45) Date of Patent: Jun. 19, 2001

(54) INHIBITION OF HAIR GROWTH

(76) Inventors: Gurpreet S. Ahluwalia, 8632 Stable View Ct., Gaithersburg, MD (US) 20879; Douglas Shander, 16112 Howard Landing Dr., Gaithersburg, MD (US) 20878

( * ) Notice: Subject to any disclaimer, the term of this patent is extended or adjusted under 35 U.S.C. 154(b) by 0 days.

(21) Appl. No.: 08/068,257

(22) Filed: May 28, 1993

(51) Int. Cl.$^7$ .......................... A61K 31/44; A61K 31/40; A61K 31/19; A61K 31/12

(52) U.S. Cl. .......................... 514/299; 514/340; 514/412; 514/423; 514/411; 514/415; 514/557; 514/567; 514/568; 514/569; 514/570; 514/682

(58) Field of Search .................................. 514/569, 299, 514/423, 567, 568, 570, 411, 415, 340, 682, 557, 412

(56) References Cited

U.S. PATENT DOCUMENTS

| | | |
|---|---|---|
| 3,426,137 | 2/1969 | Philpitt . |
| 4,039,669 | 8/1977 | Beyler et al. . |
| 4,139,638 | 2/1979 | Neri et al. . |
| 4,161,540 | 7/1979 | Neri et al. . |
| 4,191,775 | 3/1980 | Glen . |
| 4,269,831 | 5/1981 | Ferrari et al. . |
| 4,344,941 | 8/1982 | Wiechert et al. . |
| 4,370,315 | 1/1983 | Greff et al. . |
| 4,439,432 | 3/1984 | Peat . |
| 4,720,489 | * 1/1988 | Shander . |
| 4,877,789 | 10/1989 | Shroot et al. . |
| 4,885,289 | * 12/1989 | Brever et al. . |
| 5,132,293 | * 7/1992 | Shander et al. . |
| 5,189,212 | 2/1993 | Ruenitz . |
| 5,271,942 | 12/1993 | Heverhagen . |
| 5,300,284 | 4/1994 | Wiechers et al. . |
| 5,364,885 | 11/1994 | Ahluwalia et al. . |
| 5,411,991 | 5/1995 | Shander et al. . |

FOREIGN PATENT DOCUMENTS

| | | |
|---|---|---|
| 0 413 528 A1 | 2/1991 | (EP) . |
| 0 532 219 A2 | 3/1993 | (EP) . |
| 0 648 488 A1 | 4/1995 | (EP) . |
| 1 458 349 | 12/1976 | (GB) . |
| 1458349 | 12/1976 | (GB) . |
| 02017115 | 7/1988 | (JP) . |
| 1-96126 | 4/1989 | (JP) . |

OTHER PUBLICATIONS

Simpson et al., British Journal of Dermatology (1979) 100, 687.
Burdick et al., Br. J. Derm. (1970) 82, Supplement 6, 10.
Goos et al., Arch. Dermatol. Res. (1982) 273:333–341.
Girard et al., Arch. Dermatol. Res. (1980) 269:281–290.

* cited by examiner

*Primary Examiner*—Alan Siegel
(74) *Attorney, Agent, or Firm*—Fish & Richardson P.C.

(57) ABSTRACT

Mammalian hair growth is reduced by applying to the skin a composition including an inhibitor of cyclooxygenase.

34 Claims, No Drawings

INHIBITION OF HAIR GROWTH

The invention relates to the inhibition of hair growth.

Arachidonic acid is released from membrane lipids in response to injury or other irritation. The enzyme cyclooxygenase converts arachidonic acid into cyclic endoperoxides commonly known as $PGG_2$ and $PGH_2$. The endoperoxides subsequently are converted into prostoglandins, which are the primary mediators of inflammation in the body.

It has now been found that mammalian (including human) hair growth can be inhibited by applying to the skin a composition including an inhibitor of cyclooxygenase in an amount effective to reduce hair growth in the applied area.

The preferred inhibitors are commonly known as non-steroidal anti-inflammatory drugs (NSAIDs). These drugs include compounds from a variety of chemical classes.

One preferred class of NSAIDs are propionic acids, which include α-methyl-4-[2-methylpropyl]benzeneacetic acid (ibuprofen), 6-methoxy-α-methyl-2-naphthaleneacetic acid (naproxen), 2-[3-phenoxyphenyl]propionic acid (fenoprofen), 2-[3-benzoylphenyl]propionic acid (ketoprofen), gamma-oxo[1,1'-biphenyl]-4-butanoic acid (fenoprofen), and 6-chloro-α-methylcarbazole-2-acetic acid (carprofen).

Another preferred class of NSAIDs are indoleacetic acids, which include 1-[p-chlorobenzoyl]-5-methoxy-2-methylindole-3-acetic acid (indomethacin), 5-fluoro-2-methyl-1-[(4-(methylsulfinyl)phenyl) methylene]-1H-indene-3-acetic acid (sulindac), 1-methyl-5-[p-toluoyl] pyrrole-2-acetic acid (tolmetin), 2-[(2,6-dichlorophenyl) amino]benzeneacetic acid (diclofenac).

A third preferred class of NSAIDs are salicylates, which include 2-acetoxybenzoic acid (acetylsalicylic acid) and 5-[2,4-difluorophenyl]salicylic acid (diflunisal).

A fourth preferred class of NSAIDs are anthranilic acids, which include 2-[(2,6-dichloro-3-methylphenyl) amino] benzoic acid (meclofenamic acid) and 2-[(2,3-dimethylphenyl) amino]benzoic acid (mefenamic acid).

A fifth preferred class of NSAIDs are enolic acids, such as 4-hydroxy-2-methyl-N-2-pyridinyl-2H-thieno[2,3-e]-1,2-thiazine-3-carboxamide-1,1-dioxide (tenoxicam).

Other NSAIDs like 4-[6-methoxy-2-naphthyl]-2-butanone (nabumetone) also can be used.

The composition preferably includes a non-toxic dermatologically acceptable vehicle or carrier which is adapted to be spread on the skin. Examples of suitable vehicles are acetone, alcohols, or a cream, lotion, or gel which can effectively deliver the active compound. In addition, a penetration enhancer may be added to the vehicle to further enhance the effectiveness of the formulation.

The concentration of the inhibitor in the composition may be varied over a wide range up to a saturated solution, preferably from 1 to 30% by weight or even more; the reduction of hair growth increases as the amount of inhibitor applied increases per unit area of skin. The maximum amount effectively applied is limited only by the rate at which the inhibitor penetrates the skin. Generally, the effective amounts range from 100 to 3000 micrograms or more per square centimeter of skin.

The composition should be applied to the area of the body where it is desired to inhibit hair growth. Typically, the composition can be applied to the face, particularly to the beard area of the face, i.e., the cheek, neck, upper lip, and chin. The composition can also be applied to the legs, arms, torso or armpit. The composition is particularly suitable for the treatment of hirsatism. In humans, the composition should be applied once or twice a day, or even more frequently, for at least three months to achieve a perceived reduction in hair growth.

Reduction of hair growth is demonstrated when the frequency of hair removal is reduced, or the subject perceives less hair on the treated site, or quantitatively, when the weight of hair removed by shaving (i.e., hair mass) is reduced. Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster.

To evaluate the effectiveness of a particular inhibitor in reducing hair growth, the flank organs of each of a group of hamsters are depilated by applying a thioglycolate based chemical depilatory (Surgex). To one organ of each animal 10 μl. of vehicle alone once a day is applied, while to the other organ of each animal an equal amount of vehicle containing the inhibitor is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The preferred cyclooxygenase inhibitors were tested according to the above procedure. The results are presented in Table 1; the vehicles used to deliver the inhibitors are reported in Table 2.

TABLE 1

| | | | | Hair Mass | | |
|---|---|---|---|---|---|---|
| Compound | Dose | Vehicle | pH | Treated (mg) | Control (mg) | Percent Inhibition |
| Propionic acids | | | | | | |
| Ibuprofen | 20% | B | 5.0 | 1.160 ± .16 | 1.704 ± .15 | 30.33 ± 7.74 |
| Naproxen | 20% | A | 8.5 | 0.771 ± .11 | 2.108 ± .15 | 62.52 ± 5.40 |
| Fenoprofen | 20% | D | 6.0 | 0.373 ± .10 | 1.276 ± .11 | 70.58 ± 7.04 |
| Ketoprofen | 20% | B | 4.5 | 0.895 ± .20 | 1.293 ± .26 | 29.70 ± 5.10 |
| Carprofen | 20% | C | 6.0 | 0.776 ± .11 | 1.274 ± .19 | 29.69 ± 11.06 |
| Indoleacetic acids | | | | | | |

TABLE 1-continued

Hair Mass

| Compound | Dose | Vehicle | pH | Treated (mg) | Control (mg) | Percent Inhibition |
|---|---|---|---|---|---|---|
| Indomethacin | 20% | A | 8.0 | 0.307 ± .08 | 1.844 ± .28 | 83.78 ± 3.66 |
| Sulindac | 20% | A | 9.0 | 0.517 ± .09 | 2.539 ± .27 | 79.90 ± 3.27 |
| Tolmetin | 20% | A | 8.5 | 1.459 ± .16 | 2.344 ± .24 | 37.85 ± 3.35 |
| Diclofenac | 20% | B | 8.0 | 0.648 ± .10 | 1.769 ± .19 | 63.40 ± 5.21 |
| Salicylates | | | | | | |
| Acetyl-salicylic acid | 20% | B | 5.0 | 2.126 ± .33 | 3.194 ± .21 | 34.89 ± 7.91 |
| Diflunisal | 20% | D | 5.0 | 0.958 ± .10 | 1.779 ± .18 | 38.32 ± 10.73 |
| Anthranilic acids | | | | | | |
| Meclofenamic acid | 20% | A | 8.5 | 0.719 ± .14 | 2.144 ± .18 | 67.77 ± 4.79 |
| Mefenamic acid | 10% | A | 8.8 | 0.518 ± .13 | 1.520 ± .11 | 67.18 ± 6.03 |
| Enolic acids | | | | | | |
| Tenoxican | 15% | B | 8.0 | 0.326 ± .08 | 2.116 ± 0.24 | 85.38 ± 2.91 |
| Other | | | | | | |
| Nabumetone | 15% | E | 6.0 | 1.267 ± .23 | 1.684 ± .21 | 23.23 ± 10.41 |

TABLE 2

Vehicles Used in Hair Mass Assays

Vehicle A: 68% Purified water, 16% ethanol (200 proof), 5% propylene glycol, 5% dipropylene glycol, 4% benyl alcohol, 2% propylene carbonate.
Vehicle B: 80% Ethanol (190 proof), 17.5% purified water, 2% propylene glycol dipelargonate, 0.5% propylene glycol.
Vehicle C: 30% Dipropylene glycol, 25% acetone, 15% ethanol (200 proof), 10% benzyl alcohol, 10% dimethyl sulfoxide (DMSO), 10% propylene glycol.
Vehicle D: 35% Dipropylene glycol, 30% ethanol (200 proof), 20% acetone, 10% propylene glycol, 5% benzyl alcohol.
Vehicle E: 35% Dipropylene glycol, 30% ethanol (200 proof), 25% acetone, 10% benzyl alcohol.
Vehicle F: 35% Dipropylene glycol, 35% ethanol (200 proof), 15% acetone, 10% DMSO, 5% benzyl alcohol.

A preferred inhibitor, indomethacin, was tested for inhibition of hair growth in various formulations. The results are presented in Table 3.

TABLE 3

Hair Growth Inhibition by Indomethacin in Various Formulations

| Formulation | pH | Treated (mg) | Control (mg) | Percent Inhibition |
|---|---|---|---|---|
| 5% in Vehicle A | 7.5 | 1.248 ± .20 | 2.173 ± .14 | 43.41 ± 7.75 |
| 10% in Vehicle A | 7.5 | 1.084 ± .11 | 2.364 ± .22 | 53.32 ± 4.17 |
| 15% in Vehicle A | 7.5 | 0.768 ± .10 | 2.443 ± .15 | 68.77 ± 3.02 |
| 20% in Vehicle A | 8.0 | 0.307 ± .08 | 1.844 ± .28 | 83.78 ± 3.66 |
| 20% in Vehicle B | 7.0 | 0.261 ± .01 | 1.653 ± .15 | 83.37 ± 1.46 |
| 10% in Vehicle F | 5.5 | 0.679 ± .08 | 1.436 ± .20 | 49.89 ± 5.54 |
| 20% in Vehicle F | 5.5 | 0.324 ± .08 | 1.491 ± .14 | 78.43 ± 4.39 |

It will be appreciated by those skilled in the art that the invention can be performed within a wide range of equivalent parameters of composition and conditions without departing from the spirit or scope of the invention or of any embodiment thereof.

What is claimed is:

1. A process of reducing mammalian hair growth, comprising
   selecting an area of skin from which reduced hair growth is desired, and
   applying to said area of skin a composition including an inhibitor of cyclooxygenase in an amount effective to reduce hair growth.

2. The process of claim 1, wherein said inhibitor is α-methyl-4-[2-methylpropyl]benzeneacetic acid.

3. The process of claim 1, wherein said inhibitor is 6-methoxy-α-methyl-2-naphthaleneacetic acid.

4. The process of claim 1, wherein said inhibitor is 2-[3-phenoxyphenyl]propionic acid.

5. The process of claim 1, wherein said inhibitor is 2-[3-benzoylphenyl]propionic acid.

6. The process of claim 1, wherein said inhibitor is gamma-oxo-[1,1'-biphenyl]-4-butanoic acid.

7. The process of claim 1, wherein said inhibitor is 6-chloro-α-methylcarbazole-2-acetic acid.

8. The process of claim 1, wherein said inhibitor is 1-[p-chlorobenzoyl]-5-methoxy-2-methylindole-3-acetic acid.

9. The process of claim 1, wherein said inhibitor is 5-fluoro-2-methyl-1-[(4-(methylsulfinyl)phenyl)methylene]-1H-indene-3-acetic acid.

10. The process of claim 1, wherein said inhibitor is 1-methyl-5-[p-toluoyl]pyrrole-2-acetic acid.

11. The process of claim 1, wherein said inhibitor is 2-[(2,6-dichlorophenyl)amino]-benzeneacetic acid.

12. The process of claim 1, wherein said inhibitor is 2-acetoxybenzoic acid.

13. The process of claim 1, wherein said inhibitor is 5-[2,4-difluorophenyl]salicylic acid.

14. The process of claim 1, wherein said inhibitor is 2-[(2,6-dichloro-3-methylphenyl)amino]benzoic acid.

15. The process of claim 1, wherein said inhibitor is 2-[(2,3-dimethylphenyl)amino]benzoic acid.

16. The process of claim 1, wherein said inhibitor is 4-hydroxy-2-methyl-N-2-pyridinyl-2H-thieno[2,3-e]-1,2-thiazine-3-carboxamide 1,1-dioxide.

17. The process of claim 1, wherein said inhibitor is 4-[6-methoxy-2-naphthyl]-2-butanone.

18. The process of claim 1, wherein said inhibitor is a nonsteroidal anti-inflammatory drug.

19. The process of claim 18, wherein said nonsteroidal anti-inflammatory drug is a propionic acid.

20. The process of claim 18, wherein said nonsteroidal anti-inflammatory drug is an indolacetic acid.

21. The process of claim 18, wherein said nonsteroidal anti-inflammatory drug is a salicylate.

22. The process of claim 18, wherein said nonsteroidal anti-inflammatory drug is an anthranilic acid.

23. The process of claim 18, wherein said nonsteroidal anti-inflammatory drug is an enolic acid.

24. The process of claim 1, wherein said concentration of said inhibitor in said composition is between 1% and 30%.

25. The process of claim 1, wherein the composition is applied to the skin in an amount of from 100 to 3000 micrograms of said inhibitor per square centimeter of skin.

26. The process of claim 1, wherein the composition is applied to the skin on the face of said mammal.

27. A process of inhibiting mammalian hair growth, comprising applying to the skin a composition including a nonsteroidal anti-inflammatory drug.

28. The process of claim 27, wherein said nonsteroidal anti-inflammatory drug is a propionic acid.

29. The process of claim 27, wherein said nonsteroidal anti-inflammatory drug is an indoleacetic acid.

30. The process of claim 27, wherein said nonsteroidal anti-inflammatory drug is a salicylate.

31. The process of claim 27, wherein said nonsteroidal anti-inflammatory drug is an anthranilic acid.

32. The process of claim 27, wherein said nonsteroidal anti-inflammatory drug is an enolic acid.

33. The process of claim 1, wherein said composition further comprises a non-toxic dermatologically acceptable carrier.

34. The process of claim 1, wherein said composition is applied to the skin of a person suffering from hirsutism.

* * * * *

UNITED STATES PATENT AND TRADEMARK OFFICE
CERTIFICATE OF CORRECTION

PATENT NO.      : 6,248,751 B1
DATED           : June 19, 2001
INVENTOR(S)     : Gurpreet S. Ahluwalia, Ph.D. and Douglas Shander It is certified that error appears in the above-identified patent and that said Letters Patent is hereby corrected as shown below:

Title page,
Item [56], U.S. PATENT DOCUMENTS, add -- 5,095,007  3/1992  Ahluwalia --.
Add -- 5,096,911  3/1992  Ahluwalia et al. --.
Add -- 5,143,925  9/1992  Shander et al. --.

FOREIGN PATENT DOCUMENTS, delete "1458349  12/1976  (GB)".

OTHER PUBLICATIONS, add -- Sato, Biology and Disease of the Hair (1975) 3-13 --.
Add -- Laughton et al., Biochemical Pharmacology (1991) 42(9) 1673-1681 --.
Add -- Day et al., Pharmac. Ther. (1987) 33, 383-433 --.
Add -- Higgs et al., The Mode of Action of Anti-Inflammatory Drugs Which Prevent the Peroxidation of Arachidonic Acid, 675-691--.
Add -- Champion, The Medical Journal of Australia (1968) 149 --.

Signed and Sealed this

Twenty-fourth Day of December, 2002

JAMES E. ROGAN
*Director of the United States Patent and Trademark Office*